United States Patent
Gauché et al.

(10) Patent No.: US 8,999,301 B2
(45) Date of Patent: Apr. 7, 2015

(54) BLEACHING METHODS AND COMPOSITIONS

(75) Inventors: Céline Gauché, Fleet (GB); Jamie Anthony Hawkes, Leeds (GB); David Malcolm Lewis, Otley (GB)

(73) Assignee: Perachem Limited, Leeds (GB)

( * ) Notice: Subject to any disclaimer, the term of this patent is extended or adjusted under 35 U.S.C. 154(b) by 454 days.

(21) Appl. No.: 13/119,189

(22) PCT Filed: Sep. 10, 2009

(86) PCT No.: PCT/GB2009/051157
§ 371 (c)(1),
(2), (4) Date: Mar. 16, 2011

(87) PCT Pub. No.: WO2010/032030
PCT Pub. Date: Mar. 25, 2010

(65) Prior Publication Data
US 2011/0168202 A1 Jul. 14, 2011

(30) Foreign Application Priority Data

Sep. 16, 2008 (GB) .................................. 0816943.5
May 7, 2009 (GB) .................................. 0907800.7

(51) Int. Cl.
*A61Q 5/08* (2006.01)
*A61K 8/19* (2006.01)
*A61K 8/22* (2006.01)

(52) U.S. Cl.
CPC ... *A61K 8/19* (2013.01); *A61K 8/22* (2013.01); *A61Q 5/08* (2013.01)

(58) Field of Classification Search
None
See application file for complete search history.

(56) References Cited

U.S. PATENT DOCUMENTS

| 5,401,497 A | 3/1995 | Rose et al. |
| 7,887,600 B2 * | 2/2011 | Bureiko et al. ................. 8/405 |
| 2006/0246022 A1 | 11/2006 | Bureiko et al. |

FOREIGN PATENT DOCUMENTS

| EP | 1313830 B1 | 7/2005 |
| WO | 0128508 A1 | 4/2001 |

OTHER PUBLICATIONS

Patent Cooperation Treaty, PCT International Search Report and Written Opinion of the International Searching Authority for Application No. PCT/GB2009/051157 dated Jul. 6, 2010, 12 pages.

* cited by examiner

*Primary Examiner* — Jyothsna Venkat
(74) *Attorney, Agent, or Firm* — Hoffman Warnick LLC

(57) ABSTRACT

A method of treating a material, the method comprising applying to the material a composition comprising at least 10 wt % of ammonium carbonate, ammonium carbamate or a mixture thereof; and a source of hydrogen peroxide.

5 Claims, No Drawings

BLEACHING METHODS AND COMPOSITIONS

The present invention relates to methods for bleaching materials, in particular for bleaching keratinous fibre materials, for example hair.

By bleaching of a material we mean removing colour from or lightening the colour of the material.

The bleaching of human hair has been carried out for many years. In some cases it is desired to lighten the natural colour of hair. This may be because it is desired to colour the hair and a lighter initial shade is needed or it may be because a lighter colour is preferred. In some cases, bleaching of hair is used to remove colour from dyed hair.

Many methods of bleaching hair are known from the prior art. Traditional bleaching compositions include mixtures of hydrogen peroxide, sodium persulphate and ammonia.

However these compositions have a number of drawbacks, for example they can be irritating to the skin, may cause respiratory sensitisation, have a bad odour, have a poor environmental profile, give unreliable colour removal and may cause significant damage to the hair. In addition bleaching methods of the prior art are particularly inefficient at removing colour from hair which has been dyed using oxidative hair dye compositions. There is thus a need to provide alternative bleaching compositions.

One alternative method involves the use of percarbamic acid and/or a diacyl percarbamate, generated in situ by the method of the applicant's earlier patent EP 1313830B.

However, the present inventors have now developed an improved bleaching method which may be used to lighten hair.

According to a first aspect of the present invention there is provided a method of treating a material, the method comprising applying to the material a composition comprising at least 10 wt % of ammonium carbonate, ammonium carbamate or a mixture thereof; and a source of hydrogen peroxide.

Preferably the method of treating a material of the present invention is a method of bleaching the material. By this we mean to refer to a method by which colour is removed from the material.

Preferably the material treated in the method of the present invention is a keratinous material. More preferably it is a keratinous fibre material, although the method of the present invention may also be used to bleach non-fibrous keratinous based material, for example finger or toe nails. Most preferably the method of the present invention is a method of bleaching hair, in particular human hair.

The source of hydrogen peroxide may be selected from any compound which provides hydrogen peroxide or the perhydroxyl anion (HOO$^-$) in aqueous solution. Suitable sources of hydrogen peroxide include perborates, percarbonates and aqueous hydrogen peroxide solution. Where reference is made to compositions containing hydrogen peroxide, this covers compositions in which the conditions are such that the perhydroxyl ion is present.

According to a second aspect of the present invention there is provided a bleaching composition comprising at least 10 wt % of ammonium carbonate, ammonium carbamate or a mixture thereof and a source of hydrogen peroxide.

Preferably the method of the first aspect comprises applying to a material a composition of the second aspect.

It will be appreciated by the person skilled in the art than when a composition is prepared comprising the components specified it is likely that a chemical reaction will occur and thus the species present in the resultant composition will not necessarily correspond to those added originally. For the avoidance of doubt, unless explicitly mentioned otherwise in this specification any reference to any components and any amounts mentioned herein refer to components and amounts added initially in the preparation of the composition.

Preferred bleaching compositions of the present invention comprise at least 12 wt %, ammonium carbonate, ammonium carbamate or a mixture thereof, more preferably at least 14 wt %, for example at least 15 wt %.

The bleaching compositions of the present invention preferably comprise at least 16 wt % of ammonium carbonate, ammonium carbamate or a mixture thereof, for example at least 17 wt % or at least 18 wt %.

Suitably the bleaching composition comprises up to 40 wt % ammonium carbonate, ammonium carbamate or a mixture thereof, preferably up to 30 wt %, for example up to 27 wt %, more preferably up to 25 wt %, suitably up to 23 wt % and most preferably up to 22 wt %.

In especially preferred embodiments the bleaching composition comprises approximately 20 wt % ammonium carbonate, ammonium carbamate or a mixture thereof.

The bleaching composition comprises ammonium carbonate, ammonium carbamate or a mixture thereof. The mixture may be prepared from commercial sources of ammonium carbonate and/or ammonium carbamate. However it should be noted that commercial sources of ammonium carbonate often contain low levels of ammonium carbamate.

In preferred embodiments the composition of the present invention comprises ammonium carbonate.

The preferred source of hydrogen peroxide for use in the present invention is hydrogen peroxide. This may be suitably provided as an aqueous solution.

Preferably the bleaching composition comprises at least 1 wt % hydrogen peroxide, more preferably at least 2 wt %, most preferably at least 4 wt % or at least 5 wt %.

Suitably the bleaching composition comprises up to 50 wt % hydrogen peroxide, preferably up to 35 wt %, more preferably up to 25 wt %, suitably up to 20 wt %, for example up to 15 wt %, up to 12 wt % or up to 10 wt %.

Unless otherwise stated, all amounts of hydrogen peroxide mentioned in this specification are expressed as a concentration by weight of the actual $H_2O_2$ present in the composition. As will be readily understood however by the person skilled in the art, the hydrogen peroxide component itself may be provided as an aqueous composition. Any water present in this aqueous composition is not included in the amounts of hydrogen peroxide stated above and below.

Alternatively the hydrogen peroxide may be provided as a commercially available cream, paste or gel. Such compositions are usually aqueous-based and contain further components including thickeners. However the amount of hydrogen peroxide provided to the bleaching composition of the present invention when such a cream, paste or gel is used is suitably within the preferred ranges given above.

In embodiments in which the source of hydrogen peroxide is for example a perborate or a percarbonate, this is present in an amount sufficient to provide hydrogen peroxide in the amounts detailed above. Where conditions are such that the source of hydrogen peroxide provides the perhydroxyl anion, the amount of perhydroxyl ion present is suitably such that if it were converted to hydrogen peroxide it would lie within the ranges defined above.

Preferably the bleaching composition of the present invention is an aqueous composition. In some embodiments it may comprise an additional solvent for example ethanol, isopropanol, n-propanol, butanol, propylene glycol, ethylene glycol monoethyl ether, and mixtures thereof. Other suitable solvents are provided on the INCI list (International Nomenclature of Cosmetic Ingredients list). This is drawn up by the Scientific Committee on Consumer Products (SCCP) managed by the Directorate-General for Health and Consumer Protection of the European Commission. The SCCP approve a list of chemicals for use in cosmetics which is referred to as the INCI list.

The bleaching compositions of the present invention may additionally include a thickener, suitably a cosmetically approved thickener, at a level of from about 0.05 wt % to about 20 wt %, preferably from about 0.1 wt % to about 10 wt %, more preferably from about 0.5 wt % to about 5 wt %. Thickening agents suitable for use in the compositions herein include those specified for cosmetic use on the INCI list. Preferred thickening agents suitable for use in the compositions of the present invention include oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22®, steareth-20 methacrylate copolymer; Aculyn 44®, polyurethane resin and Acusol 830®, acrylates copolymer which are available from Rohm and Haas, Philadelphia, Pa., USA. Additional thickening agents suitable for use in the bleaching compositions of the invention include sodium alginate or gum arabic, or cellulose derivatives, such as methyl cellulose or the sodium salt of carboxymethylcellulose or some types of acrylic polymers The bleaching composition may further comprise one or more ingredients selected from fragrances, stabilisers, antimicrobials, conditioners, emulsion stabilisers, film formers, emulsifiers, antioxidants, chelators, antistatic agents, anticaking agents, buffers, bulking agents, UV absorbers, moisturising agents, opacifiers, masking agents, reducing agents, humectants, foaming agents. Each of these components may be selected from the INCI list. In some preferred embodiments the bleaching composition further comprises a conditioning agent. Preferred conditioning agents include cetyl trimethyl ammonium chloride and cetyl trimethyl ammonium bromide.

Preferably the bleaching composition has a pH of from 6 to 13, more preferably 7 to 12, more preferably from 8 to 11, for example from 9 to 10.5 or especially from 9.5. to 10.

The bleaching composition of the present invention is preferably not a hair colouring composition. By this we mean that the composition does not add colour to the hair. Rather the application of the composition to hair causes a lightening of the colour of the hair. Thus the composition of the present invention preferably does not include a colouring agent, dye or other chromophore. Hence the composition of the present invention is preferably substantially free of dye compounds.

However in some embodiments the bleaching composition may comprise a colour masking agent. Suitable colour masking agents include carbon black or other non-substantive colours for example polymeric colours or pigments. A colour masking agent may be added so that when a person's hair is being lightened by the bleaching composition of the invention, for example in a salon, they do not readily realise the extent to which the hair has been lightened. This may be useful if the hair is to be dyed immediately afterwards. Consumers associate hair lightening with hair damage and thus if they observe a very light colour prior to subsequent dyeing they may believe the hair to be damaged, even though the bleaching method of the present invention is very mild.

The bleaching composition may be provided in any suitable form. Preferably it is provided as a cream, gel or paste such that it can be easily applied to the material for example hair and will not run off. Other suitable forms will be known to the person skilled in the art.

Preferably in the method of the present invention the bleaching composition is applied to the material and left on the material for a period of time before rinsing with water.

Suitably the bleaching composition is left on the material for a period of up to 90 minutes, for example up to 60 minutes, suitably up to 50 minutes, preferably up to 40 minutes.

The composition is preferably left on the material for a period of at least 1 minute, preferably at least 5 minutes, for example at least 10 minutes, suitably at least 15 minutes.

Preferably the composition is left on the material at a temperature of from 10 to 60 more preferably from 20 to 50 for example from 30° C. to 45° C. When at temperatures above ambient temperature and the material is human hair a suitable hood can be employed to achieve the required temperature.

The extent of the bleaching effect achieved may be dependent on the concentration of the components present, the time for which the composition is left on the material and the temperature at which the treatment is carried out. In some cases a lighter shade may be desired than in other cases and thus appropriate variation of these conditions may be made. For example it has been found that if the bleaching composition of the present invention is left on human hair for 45 minutes or longer very white hair can be achieved.

Preferably following treatment of the hair or other material for the required period, the bleaching composition is removed from the material. This may be carried out for example by rinsing with water.

Preferably the bleaching composition used in the method of the present invention is freshly prepared prior to application by mixing together a first precursor composition comprising ammonium carbonate, ammonium carbamate or a mixture thereof and a second precursor composition comprising a source of hydrogen peroxide. The above definitions of amounts etc. relate to the resultant active bleaching composition that is applied to the hair.

The present invention may further provide a bleaching kit comprising a first precursor composition comprising ammonium carbonate, ammonium carbamate or a mixture thereof and a second precursor composition comprising a source of hydrogen peroxide. Each precursor composition may comprise one or more of the further ingredients mentioned herein. Preferably each precursor composition is an aqueous composition although embodiments in which the or each precursor composition is provided as a solid are also within the scope of the invention.

For example a bleaching kit could be provided containing a solid source of peroxide such as percarbonate or perborate; and ammonium carbonate and/or ammonium carbamate as a solid; along with instructions to dissolve these components and optional further ingredients in a suitable amount of water prior to application to the material (e.g. hair). A graduated mixing pot of the appropriate size could optionally be provided.

The precursor compositions may each be provided in any suitable form, for example a solid, liquid, paste or gel. However in preferred embodiments the bleaching composition of the second aspect, which is formed upon admixture of said precursor compositions, preferably has a viscosity which enables it to be easily applied to the hair but does not run off.

Each precursor composition of the bleaching kit of the present invention may comprise part of a bi-component thickening system such that mixing of the two precursor compositions provides a bleaching composition of increased viscosity. A thickener which undergoes a change in viscosity upon a change in pH could also be included.

The properties sought in a thickener system are those which provide the composition with a suitable viscosity profile in order for it to spread across the head easily during the hair bleaching process, and then stay in position on the head when required. The choice of thickening agent or bi-component thickening agent is dependent on the additional components within a composition, and such choices are well known to those skilled in the art. Suitable materials can be found on the INCI list.

Further features of the bleaching kit comprising a first precursor composition and a second precursor composition are described later in this specification in relation to the packaged hair bleaching product.

The present inventors have found that the use of the bleaching composition and method of the present invention provides a mild but effective bleaching of natural melanin pigment which causes reduced damage to the hair compared with bleaching compositions of the prior art. In particular the bleaching composition and method of the present invention show significant advantages over compositions of the prior art containing hydrogen peroxide and sodium persulphate ($Na_2S_2O_8$) which are set at approximately pH10 using ammonium hydroxide. The method and composition of the present invention allow bleaching to be effected without the use of ammonia or persulfate. Of great advantage is the minimal hair damage observed and the rapid nature of the process.

Indeed the hair bleaching method the present invention is so mild that it can be repeated. Thus the same sample of hair may be dyed two or even more times using the bleaching method of the present invention. This represents a considerable improvement over bleaching methods of the prior art where bleaching more than once can cause the hair to break or dissolve.

Without wishing to be bound by any theory, it is believed that the active bleaching agent present in the bleaching composition of the present invention is percarbamic acid. When ammonium carbamate is used, this reacts slowly with hydrogen peroxide to generate percarbamic acid in a controlled manner.

When ammonium carbonate is used it is believed that percarbamic acid is again the active bleaching agent. An equilibrium between ammonium carbonate and carbamic acid may be formed in solution according to the following reaction scheme:

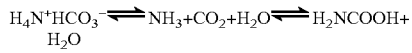

Carbamic acid can then be converted to percarbamic acid, the active bleaching species by reaction with hydrogen peroxide according to the reaction scheme:

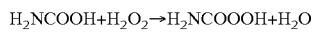

Because the active bleaching agent is provided in a controlled manner in the compositions of the present invention, bleaching can be achieved with maximum effectiveness and minimum damage.

It has previously been suggested that percarbonic acid is the active bleaching agent in compositions comprising ammonium carbonate and peroxide (see, for example, Marsh, J; Gummer, C; Dahlgren, M; Novel permanent hair colouring, J. of Cosmetic Science, vol 58, No. 1, January/February 2007; Annual Scientific Meeting 2006 p 88-89). However the present inventors believe this not to be the case since when ammonium carbonate was replaced by lithium carbonate no such enhanced bleaching effect was observed.

Free ammonia and free carbon dioxide will always become available as decomposition of ammonium carbonate occurs. Their relative concentrations are dependant on the pH of the solution—the more acidic the greater the amount of free $CO_2$ electrophile and conversely the more alkaline the greater the concentration of free $NH_3$ nucleophile. These components can react as detailed above to form carbamic acid in situ.

It is believed to be the above pH effects which determine the rate of formation and amount of carbamic acid in the solution and thence percarbamic acid production in the bleaching process—if the percarbamic acid is formed too quickly then the amount of highly active bleaching agent is too high and hair damage may occur.

In some embodiments the present invention may involve the use of a pre-treatment step prior to application of the bleaching composition of the second aspect. The use of such a pre-treatment step is particularly effective if it is desired to remove colour from dyed hair in particular hair which has been dyed using an oxidative dye. Most commonly used hair dyes that are currently available are oxidative dyes that are known to be very difficult to remove from the hair once they have been applied, especially when dark shades are used.

According to a third aspect of the present invention there is provided a method of treating a material, the method comprising the steps of:

(a) applying to the material a pre-treatment composition comprising a thiol or a salt thereof; and
(b) applying to the material a bleaching composition of the second aspect.

Preferably in the method of the third aspect there is a step in between step (a) and step (b) of removing the composition applied in step (a) from the hair. This is suitably carried out by rinsing the composition from the hair with water.

The pre-treatment composition comprises a thiol or a salt thereof. This is preferably present in an amount of at least 0.1 wt %, preferably at least 1 wt %, for example at least 1.25 wt % or at least 1.5 wt %. It may be present in an amount of up to 10 wt %, for example up to 7.5 wt %, suitably up to 5 wt %, preferably up to 4 wt %, for example up to 3 wt % or up to 2.5 wt %.

In the case where the thiol is provided as a salt the above amount referred to the equivalent amount that would be present as the free acid.

When a salt of a thiol is present, this is preferably a water-soluble salt. Preferred salts are alkali metal or ammonium salts. Most preferred are potassium and especially sodium salts.

Preferred thiols for use in step (a) include thioglycolic acid, thiolactic acid, dihydrolipoate, thioglycerol, mercaptopropionic acid, cysteine, N-substituted cysteines, cysteamines, N-substituted cysteamines, thioethanol and 1-thiopropane 3-sulfonate.

In especially preferred embodiments the thiol used in step (a) is thioglycolic acid or a salt thereof.

Preferably the pre-treatment composition of the present invention has a pH of between 1 and 9, preferably between 2 and 8, for example between 3 and 7 or more preferably between 4 and 6.

Preferably the pre-treatment composition of the present invention includes a base, preferably a cosmetically approved base. Preferred bases for use herein include those detailed on the INCI list. One such suitable base for use in the pre-treatment composition of the present invention is 2-amino-2-methyl-1-propanol.

Suitably the pre-treatment composition comprises at least 0.1 wt % base, preferably at least 0.5 wt %, more preferably at least 0.75 wt %, for example at least 1 wt %, more preferably at least 1.25 wt %.

Suitably the pre-treatment composition comprises a base in amount of up to 10 wt %, preferably up to 7.5 wt %, suitably up to 5 wt %, for example up to 3 wt % or up to 2 wt %.

Suitably the pre-treatment composition used in the present invention further comprises urea. Urea may be present in an amount of at least 1 wt %, preferably at least 3 wt %, for example at least 5 wt % or at least 7 wt %. Suitably urea is present in an amount of up to 25 wt %, for example up to 20 wt %, suitably up to 15 wt %, for example up to 12 wt % or up to 10 wt %.

Preferably the pre-treatment composition is an aqueous composition. In some embodiments it may comprise an additional solvent for example ethanol, isopropanol, n-propanol, butanol, propylene glycol, ethylene glycol monoethyl ether, and mixtures thereof. Other suitable solvents are provided on the INCI list (International Nomenclature of Cosmetic Ingredients list).

The pre-treatment composition may further comprise one or more ingredients selected from fragrances, stabilisers, antimicrobials, conditioners, emulsion stabilisers, film formers, emulsifiers, antioxidants, chelators, antistatic agents, anti-caking agents, buffers, bulking agents, UV absorbers, moisturising agents, opacifiers, masking agents, reducing agents, humectants, foaming agents. Each of these components may be selected from the INCI list.

The present invention further provides a pre-treatment composition as defined herein. Such a composition suitably comprises thioglycolic acid, urea, a base and water.

The pre-treatment composition may further comprise a thickener. An appropriate thickener may be selected to provide the desired viscosity profile. The selection of an appropriate thickener is within the competence of the person skilled in the art. Preferred thickeners are detailed on the INCI list.

Preferably the pre-treatment composition is provided in the form of a gel, lotion or paste which can be easily applied to the material, suitably human hair growing on the head, but will remain in position for the desired treatment period.

In step (a) of the present invention the pre-treatment composition is preferably left on the hair for at least one minute, preferably at least 3 minutes, suitably at least 5 minutes, more preferably at least 7 minutes, for example at least 10 minutes. The pre-treatment composition may left on the hair for a period of up to 90 minutes, suitably up to 60 minutes, preferably up to 50 for example up to 40 minutes, up to 30 minutes or up to 25 minutes.

Preferably the pre-treatment composition is left on the hair at a temperature of from 10° C. to 60° C., for example from 20° C. to 50° C., suitably from 30° C. to 45° C.

Following this period the composition is suitably removed from the hair, for example by rinsing with water.

During both treatment steps (a) and (b), the material being treated may be covered after the pre-treatment or bleaching composition has been applied. This will help prevent evaporation or degradation of the composition and ensure that an even bleaching is achieved.

Suitably during step (a) the treated material may be covered with a plastics material, for example cling film. Suitably during step (b) the material may be covered with a reflective material for example foil.

The method of the present invention may be used to bleach some or all of the hair on a human head. Thus all of the hair on the head could be lightened. Alternatively, small sections of the hair could be bleached to provide "streaks" or "highlights". The present invention could be used to bleach only new hair at the roots if the remaining hair has already been lightened. All of these techniques are well know to the person skilled in the art.

The invention may also provide a hair treatment kit comprising a pre-treatment composition and a bleaching composition of the second aspect. As previously stated the bleaching composition may be provided as a bleaching kit comprising a first precursor composition and a second precursor composition. Thus the present invention may provide a kit may comprise a pre-treatment composition, a first precursor bleaching composition, and a second precursor bleaching composition. Such a hair treatment kit may further comprise instructions for use.

According to a fourth aspect of the present invention there is provided the use of a composition comprising ammonium carbonate, ammonium carbamate or a mixture thereof and hydrogen peroxide to bleach a material.

A further aspect of the present invention provides a packaged hair bleaching product comprising means for providing a bleaching composition of the second aspect and instructions for using said composition for bleaching human hair.

The packaged hair bleaching product may comprise a premixed bleaching composition of second aspect comprising ammonium carbonate, ammonium carbamate or a mixture thereof; and hydrogen peroxide. Alternatively it may comprise a bleaching kit comprising a first precursor composition and a second precursor composition as previously described herein. In some embodiments the packaged hair bleaching product may further comprise a pre-treatment composition as previously described herein along with instructions for use. The packaged hair bleaching product may further comprise instructions for preparing the active bleaching composition of the second aspect.

In some embodiments in which the packaged bleaching product comprises a bleaching kit comprising first and second precursor compositions these may be provided in bicompartment container in which the first precursor composition is held in a first compartment and the second precursor composition is held in a second compartment, of the same container. Preferably the bicompartment container is arranged to deliver the first and second precursor compositions to the same locus. This may be achieved by providing adjacent outlets from the first and second compartments. Alternatively, the first and second compartments may deliver the first and second precursor compositions into a common passageway in which they are contacted prior to exiting the container through a single outlet. Bicompartment containers of this type are known to the person skilled in the art. One such example is a squeezable tube (known as a "dual tube") having two compartments comprising the two precursor compositions. Squeezing the tube causes the two compositions to be delivered through adjacent outlets such that they are immediately contacted on their release from the container. Other embodiments of bicompartment containers include bottles or canisters for holding mousses, gels or sprays which are provided with a single actuator which effects delivery of the two precursor compositions to the same locus via the same or adjacent outlets.

Alternatively the bleaching kit of the present invention may be provided as two discrete precursor compositions which are packaged separately in individual containers. In such embodiments, the packaged hair bleaching product may further comprise instructions for preparing the active bleaching composition of the second aspect.

In some embodiments the packaged hair bleaching product may further comprise a utensil for application of the bleaching and/or pre-treatment composition to the hair, for example a brush or a spatula. In some embodiments the packaged product may further comprise equipment for preparing the bleaching composition, for example a container and/or stirrer.

Where appropriate any feature of any aspect of the present invention may be combined with any feature of any other aspect.

The invention will now be further defined with reference to the following non-limiting examples:

EXAMPLE 1

Natural hair dyed red using an oxidative hair dye (from Clairol Herbal Essence) was treated with a pre-treatment composition comprising the following ingredients:

| | |
|---|---|
| urea | 8.79 wt % |
| thioglycolic acid | 1.76 wt % |
| 2-amino-2-methyl-1-propanol | 1.51 wt % |
| water | 87.94 wt % |
| Total | 100.00 wt % |

The composition had a pH of 5.

The hair was thoroughly wetted with the solution (2.5 mL per 1 g hair), covered with cling film and left at 40° C. for 15 min.

The hair was then rinsed thoroughly with warm water.

A bleaching composition comprising the following components was then applied to the hair.

| | |
|---|---|
| Ammonium carbonate | 20 wt % |
| $H_2O_2$ (12 wt % cream formulation) | 80 wt % |
| Total | 100 wt % |

The bleaching composition has a pH of 10 and was provided in the form of a cream. The cream was brushed onto the hair, wrapped in foil and left for 30 min at 40° C. After this period the composition was removed by rinsing with water.

The resulting hair was very pale blond in colour.

In a comparative test a sample of the same dyed hair was treated with a commercial bleaching composition of the prior art, available from Goldwell and sold as a "Colour Removal System". A 45 minute treatment was followed according to the manufacturer's instructions. However the resultant hair had the same colour as before the bleaching step only a slightly lighter shade.

EXAMPLE 2

A sample of natural undyed hair having an initial medium brown appearance was treated as follows.

| Part 1 | | Part 2 | |
|---|---|---|---|
| 100% | Ammonium carbonate | 97.60% | $H_2O_2$ (9% Soln) |
| | | 1.00% | Laurylamidopropylbetaine |
| | | 1.40% | Aculyn 22 |

Aculyn 22® is a cosmetically approved thickener available from Rohm and Haas and comprises a hydrophobically modified alkali-soluble emulsion polymer.

Percentage values in the table above denote the weight of a given component expressed as a percentage of the total weight of the composition of the part in which it is present.

The hair treatment mixture was prepared by mixing 2.0 g of Part 1 and 11.0 g of Part 2.

The mixture was brushed into the hair and left at 30° C. for 20 minutes using a liquor ratio of 2.5:1 (2.5 g of preparation mixture: 1 g hair tress).

The hair was then rinsed with cold or warm water and dried.

The resulting hair was a bleached blond colour with little or no damage.

The invention claimed is:

1. A method of bleaching human hair, the method comprising applying to the human hair a composition comprising from 14 to 27 wt % of ammonium carbonate, ammonium carbamate or a mixture thereof; and a source of hydrogen peroxide.

2. A method of bleaching human hair, the method comprising the steps of:
   (a) applying to the human hair a pre-treatment composition comprising a thiol or a salt thereof; and
   (b) applying to the human hair a bleaching composition comprising from 14 to 27 wt % of ammonium carbonate, ammonium carbamate or a mixture thereof; and a source of hydrogen peroxide.

3. A method according to claim 2 which includes a step in between step (a) and step (b) of removing the pre-treatment composition applied in step (a) from the hair.

4. A method according to claim 2 wherein the pre-treatment composition comprises thioglycolic acid or a salt thereof.

5. A method according to claim 4 wherein the pre-treatment composition further comprises urea and/or a base.

* * * * *